(12) United States Patent
Thoms et al.

(10) Patent No.: US 6,803,125 B2
(45) Date of Patent: Oct. 12, 2004

(54) LIGHT EMISSIVE MATERIALS INCORPORATING QUINOLINOLATO METAL COMPLEXES

(75) Inventors: Travis P. S. Thoms, San Lorenzo, CA (US); Jiang-Ping Chen, San Jose, CA (US); Bing R. Hsieh, Webster, NY (US)

(73) Assignee: Canon Kabushiki Kaisha, Tokyo (JP)

( * ) Notice: Subject to any disclaimer, the term of this patent is extended or adjusted under 35 U.S.C. 154(b) by 14 days.

(21) Appl. No.: 10/162,581

(22) Filed: Jun. 6, 2002

(65) Prior Publication Data

US 2003/0230738 A1 Dec. 18, 2003

(51) Int. Cl.$^7$ .......... H05B 33/14; C09K 11/06; C07D 401/00
(52) U.S. Cl. .......... 428/690; 428/917; 313/504; 546/7; 546/56
(58) Field of Search .......... 428/690, 917; 313/504; 252/301.16; 546/7, 56

(56) References Cited

U.S. PATENT DOCUMENTS

| | | | |
|---|---|---|---|
| 5,151,629 A | 9/1992 | VanSlyke | 313/504 |
| 5,294,869 A | 3/1994 | Tang et al. | 313/504 |
| 5,405,709 A | 4/1995 | Littman et al. | 428/690 |
| 5,466,392 A | 11/1995 | Hironaka et al. | 252/301.16 |
| 5,552,547 A * | 9/1996 | Shi | 546/7 |
| 6,001,284 A | 12/1999 | Enokida et al. | 252/583 |
| 6,091,382 A | 7/2000 | Shioya et al. | 345/76 |
| 6,203,933 B1 | 3/2001 | Nakaya et al. | 428/690 |
| 6,451,455 B1 * | 9/2002 | Thompson et al. | 428/690 |

FOREIGN PATENT DOCUMENTS

EP  0 992 564 A1 * 4/2000

OTHER PUBLICATIONS

Chen, C. H., et al., "Recent Developments in Molecular Organic Electroluminescent Materials", Macromolecular Symposia, Am. Chem. Soc., Meeting Apr., 13–15, 1997, pp. 1–48, published Jan. 1998.

Koene, B. E., et al., "Asymmetric Triaryldiamines as Thermally Stable Hole Transporting Layers for Organic Light-Emitting Devices", Chem. Mater., Aug. 1998, vol. 10, pp. 2235–2250.

Liu, P., et al. "Luminescence Properties of Novel Soluble Quinacridones," Journal of Photochemistry and Photobiology A: Chemistry, 137 pp. 99–104 (2000).

C. W. Tang, et al., "Electroluminescence of Doped Organic Thin Films", J. Appl. Phys., vol. 65, No. 9, May 1, 1989, pgs. 3610–3616.

* cited by examiner

*Primary Examiner*—Marie Yamnitzky
(74) *Attorney, Agent, or Firm*—Fitzpatrick, Cella, Harper & Scinto

(57) ABSTRACT

Novel emissive materials suitable for organic light emitting devices are disclosed having a structure $(L_2M)_n$—X wherein L is a 2-alkyl-8-quinolinolate or 2-phenyl-8-quinolinolate ligand, M is a trivalent metal atom, n is an integer between 1 and 12. When n equals 1, X comprises a monovalent arylate emitter that contains at least one triarylamine group or a light emitting group with emission peak wavelength in the range of 500–750 nm. When n equals 2, X comprises a divalent arylate emitter that contains at least one triarylamine group or a light emitting group with emission peak wavelength in the range of 500–750 nm. When $3 \leq n \leq 12$, X is an n-valent arylate group.

2 Claims, No Drawings

LIGHT EMISSIVE MATERIALS INCORPORATING QUINOLINOLATO METAL COMPLEXES

BACKGROUND OF THE INVENTION

1. Field of the Invention

The present invention is directed to light emissive materials incorporating quinolinolato metal complexes used as emissive materials in electroluminescent (EL) devices, and in particular organic light emitting devices (OLEDs). These devices have utility, for example, in flat panel displays.

2. Description of the Related Art

OLEDs are typically comprised of at least a layer of emissive material sandwiched between an anode, typically comprised of a transparent conductor such as indium-tin oxide, and a cathode, typically a low work-function metal, such as magnesium, calcium, aluminum, or the alloys thereof. When a bias is applied across the electrodes, positive charges (holes) and negative charges (electrons) are respectively injected from the anode and cathode into the emissive layer. The holes and the electrons form excitons in the emissive layer which emit light. Hole transport layers and electron transport layers may also be added adjacent the respective electrodes to facilitate charge transfer. Depending upon whether hole transport or electron transport is favored, the light emissive layer may be located closer to the anode or the cathode. In some instances, the emissive layer is located within the hole transport or electron transport layer. Known arrangements of electrodes, hole transport layers, electron transport layers and emissive layers in multilayer structures are disclosed for example in B. R. Hsieh, Ed., "Organic Light Emitting Materials and Devices," Macromolecular Symposia, 125, 1–48 (1997), which is incorporated herein by reference.

Tris(8-hydroxyquinoline)aluminum (AlQ$_3$) complex is a widely studied emissive aluminum complex having the following structure:

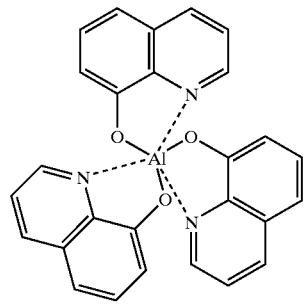

AlQ$_3$ which has a characteristic green emission with a wavelength of about 535 nm, may be doped with guest emitter compounds to prepare an emissive system having an emission spectrum close to that of the guest. The emitter is energized by direct excitation or by transfer from the AlQ$_3$ host. Examples of these systems are described in C. W. Tang, et al., J. Appl. Phys., 65, 3610 (1989), which is also incorporated herein by reference.

Conventional doping causes certain problems. For example, if the guest compounds do not disperse properly in the matrix, "aggregation" occurs, local areas of high concentration of the guest compound which in turn leads to "quenching," a phenomenon in which the guest compound absorbs energy but fails to emit at its characteristic wavelength or desired intensity.

AlQ3 has also become the prototype for a class of photoemitting materials in which quinolinolato metal complexes are bonded to organic groups. Examples of this class of materials are disclosed in U.S. Pat. Nos. 5,466,392 and 5,294,869, which are also incorporated herein by reference. Some of these materials show promise for use as emissive layers in OLEDs, exhibiting properties such as good electron transport, photoemission, high thermal stability, solubility and ease of sublimation. However, these photoemitting materials do not luminesce at wavelengths characteristic of the organic groups bonded to the metal complexes. Instead the organic groups merely modify or shift the emission of the metal complex portion of the material. While some of the organic modifying groups disclosed in the aforesaid U.S. Pat. Nos. 5,466,392, and 5,294,869 may have weak emission spectra, most of them are not light emitting at all.

The inventors herein have discovered materials based on the bonding of modified quinolinolate ligands to light emitting arylates, which exhibit photoemissive and charge transport properties, and which can reduce or eliminate the necessity for doping to improve emission efficiency or color in an organic light emitting device. In preferred embodiments, these materials exhibit emission spectra close to the characteristic emission spectra of the contained light-emitting arylate. In these instances, the metal complex serves to activate the emission of the light-emitting arylate, without contributing substantially to emission.

SUMMARY OF THE INVENTION

The invention is a light emissive material suitable for use in an OLED with a structure (L$_2$M)$_n$—X wherein L is a 2-alkyl-8-quinolinolate or 2-phenyl-8-quinolinolate ligand, M is a trivalent metal atom complexed with the ligand to form a conjugated metal complex, and n is an integer between 1 and 12. When n is equal to 1 or 2, X comprises a monovalent or divalent arylate emitter, respectively, that contains at least one arylamine group, or which is conjugation-isolated from the metal complex. When $3 \leq n \leq 12$, X is an n-valent light emitting arylate group.

In embodiments, when n is equal to 1 or 2, X is a light emitting group having an emission in the range of about 500 nm to about 750 nm. Emission at this wavelength is necessary to obtain energy transfer from the metal complex. Provided the emitter's characteristic wavelength of emission is high enough (between about 500 nm and about 750 nm), the characteristic emission of the combined complex-plus-emitter will be at the characteristic emission wavelength of the emitter. In other embodiments, the complexes according to the invention comprise an amine or alkane functionality isolating the conjugation of the arylate emitter from the conjugation of the metal complex.

The invention in a further aspect is embodied as a multivalent arylate emitter core bonding to 3 to 12 metal quinolinolate complexes according to the following structure:

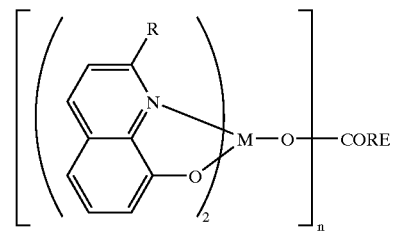

where "M" is a trivalent metal and "core" is a multivalent moiety such as:

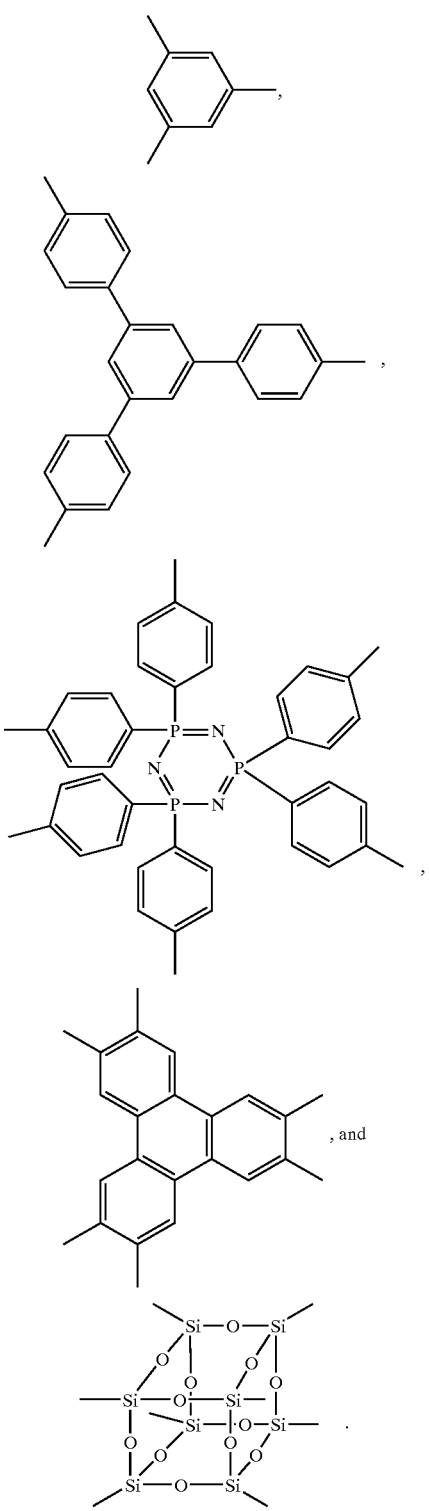

This brief summary has been provided so that the nature of the invention may be understood quickly. A more complete understanding of the invention can be obtained by reference to the following detailed description of the preferred embodiments thereof in connection with the attached drawings.

DETAILED DESCRIPTION OF THE PREFERRED EMBODIMENTS

The ligands used in the present invention are 2-alkyl-8-quinolinolate or 2-phenyl-8-quinolinolate ligands having the following structure:

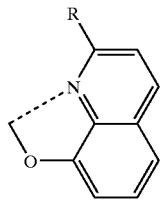

where R is substituted or unsubstituted branched or straight chain alkyl, such as, without limitation methyl, ethyl, propyl or butyl, or substituted or unsubstituted aryl, such as, without limitation, phenyl. The ligand(s) L are complexed with metal M bonded to light emitting group X according to the formula $(L_2M)_n$—X. Complexing of the metal atom takes place with the electron density associated with the nitrogen and oxygen atoms of the ligand (coordinate and covalent bonds respectively). Metal complexes of quinolinolate ligands generally emit in the green region of the spectrum.

M is a trivalent metal, preferably aluminum.

"Light emitting group" and "emitter" are used interchangeably herein to mean any group in the recited combination which exhibits fluorescent or phosphorescent emission in the visible spectrum upon relaxation from an excited state. Thus, in the formula $(L_2M)_n$—X, both $L_2M$ and X are capable of being emitters. In preferred embodiments, the metal complex $L_2M$, although capable of emission, does not emit light upon relaxation from the excited state, but transfers energy to the arylate emitter X, and X is substantially the sole emitter. In other embodiments X is a very weak emitter, and is provided mainly as a core on which the quinolinolate complexes are attached. In these embodiments emission of the material is at a wave length of the metal complex.

The entire group X is referred to as the emitter, even though only a small portion of X contains the functional groups responsible for emissive transition. In every case X contains an arylate group whose oxygen atom is bonded to the metal. This structure is required to have a stable bond to the metal complex. X may also contain bridging groups between the arylate moiety bonded to the metal and the rest of the arylate emitter. Such bridging groups isolate the conjugation of the arylate emitter from the conjugation of the metal complex, causing the emissive material to emit at a characteristic wavelength of the arylate emitter. The arylate bonded to the metal and the bridging groups are not themselves emissive, nevertheless, they form a part of X, the entirety of which is referred to as the arylate emitter.

Examples of isolating groups include —$CH_2$—, —$CH_2$—$CH_2$—, —$ArOCH_2$—, —$Ar_2N$—$R_2N$—, —$Si$—$CH_2$—, and the like.

In the formula $(L_2M)_n$—X, where n is equal to 1, arylate emitters may include the following:

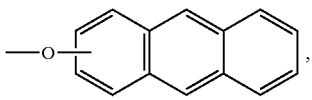

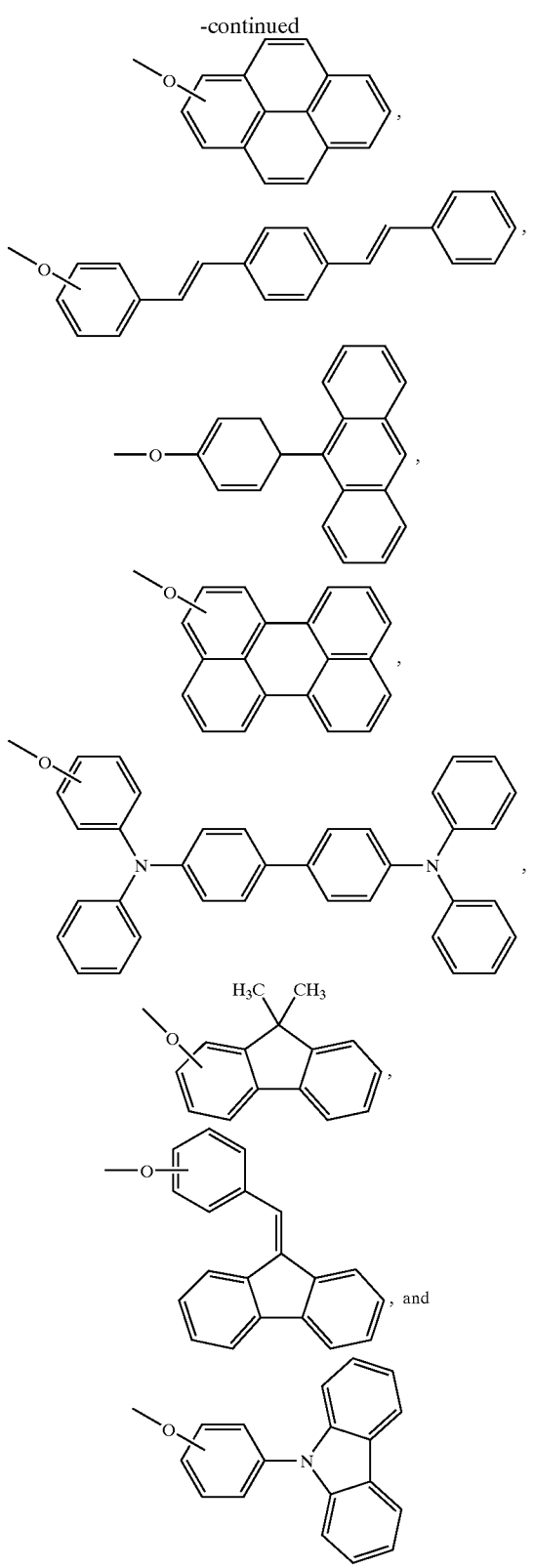

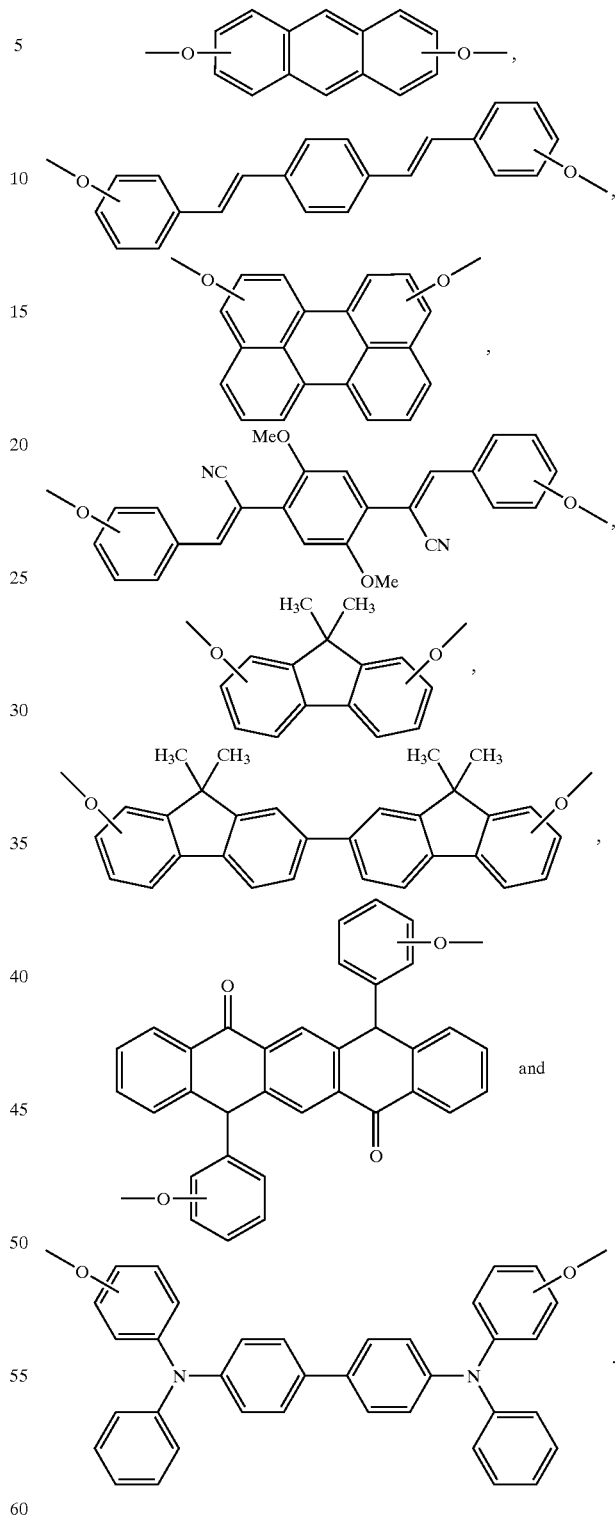

In the formula $(L_2M)_n$—X, where n is equal to 2, and divalent arylate emitters may comprise the following:

all of which have emission in the blue or blue-violet region of the visible spectrum.

While referred to as "emitters" in the context of this disclosure, the above arylates do not cause the emissive material $(L_2M)_n$—X to emit at a characteristic wavelength of these groups. These X groups serve as a core on which quinolinolate complexes are attached.

Examples of an emissive material according to formula $(L_2M)_n$—X, where n equals 2 and X is an arylate emitter incorporating arylamine groups include the following:

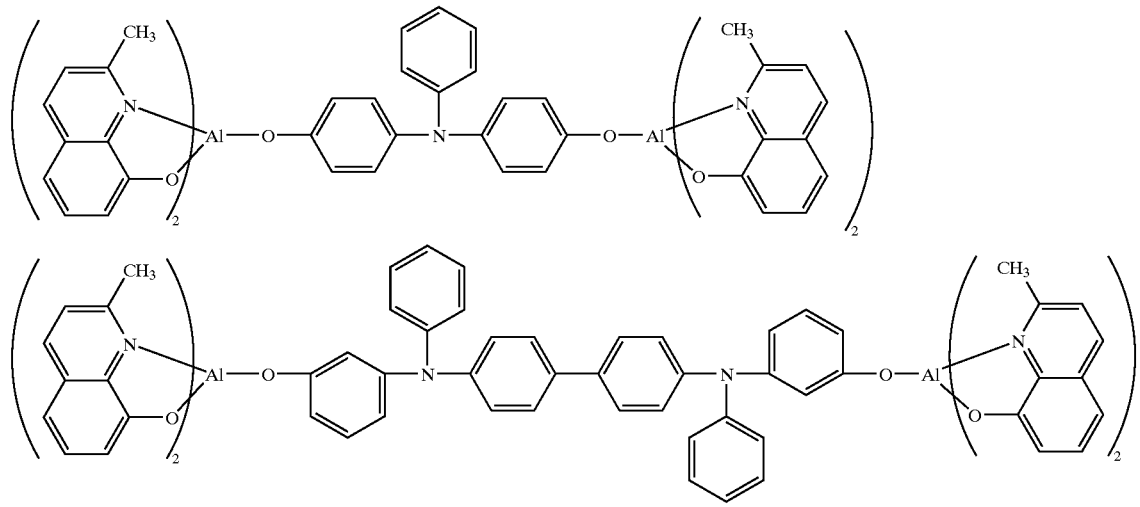

The methyl groups on the modified quinolinolate ligands can be replaced by phenyl groups and still remain within the scope of the invention. Likewise, additional triarylamine groups can be added to the arylate emitter X without departing from the scope of the invention. In general, triarylamine is a weak emitter. Accordingly, in embodiments where the arylate emitter X consists essentially of one or more triarylamine groups, the function of the triarylamine group(s) is primarily to impart hole-transport capability to the emissive material. One of ordinary skill in the art will appreciate that $AlQ_3$ itself has electron-transport capability. The triarylamine group may also shift the wavelength of the emission of the metal complex, however, the emission of the emissive material will not be the characteristic triarylamine emission wavelength.

An example of preparing an emissive material according to formula $(L_2M)_n$—X, where n is equal to 2 and having amine bridging group isolating the conjugation of the metal complex from the conjugation of the arylate emitter, is given in Scheme 1 below.

Scheme 1

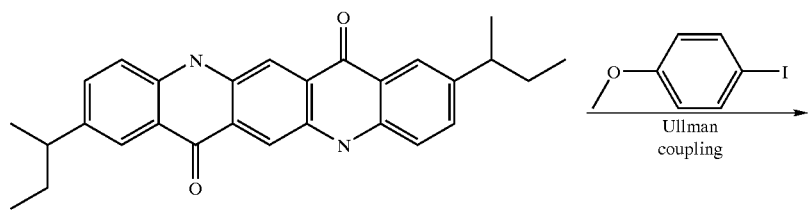

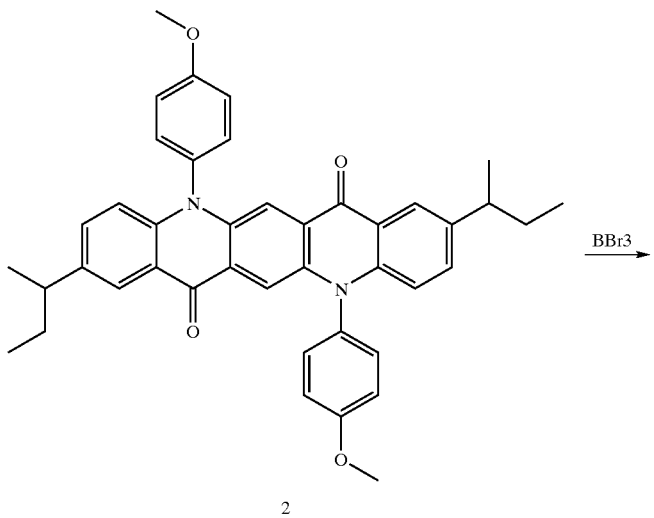

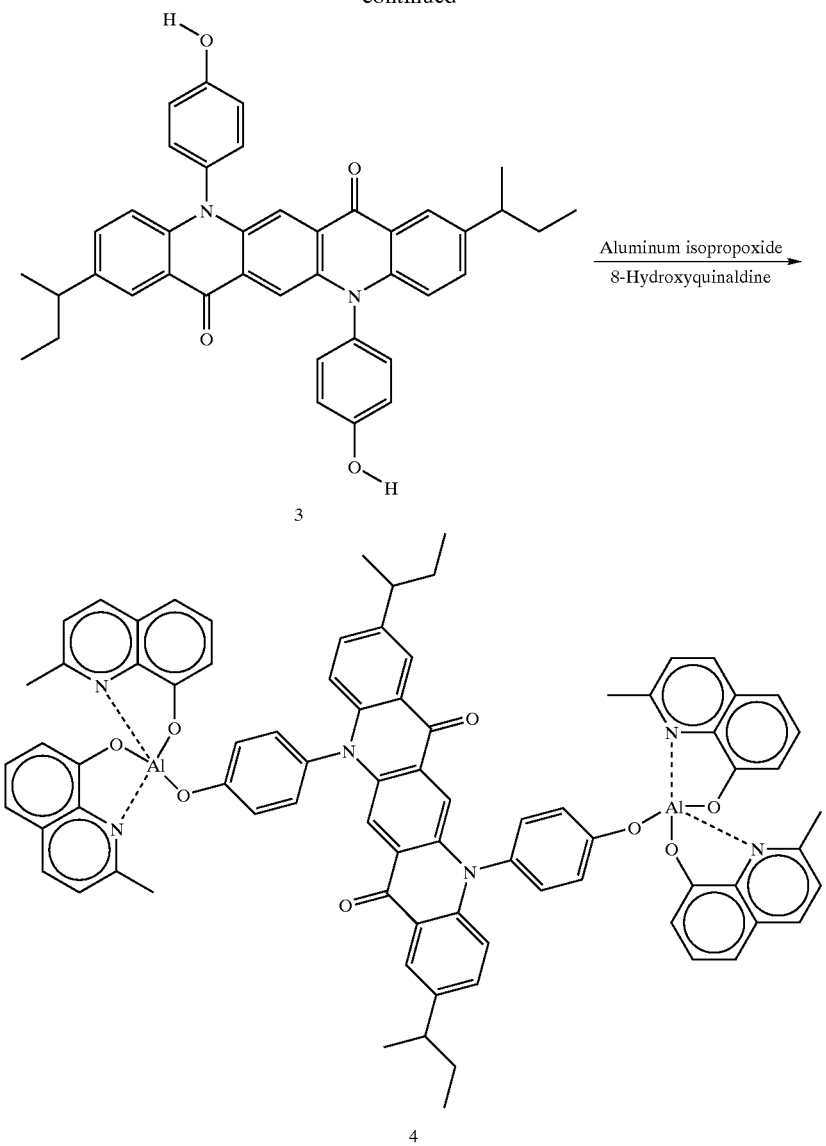

Compound 1 is a quinacridone derivative, which can be prepared according to methods set forth by Pei-Hua Liu, et al., "Luminescence Properties of Novel Soluble Quinacridones," Journal of Photochemistry and Photobiology A: Chemistry 137 (2000) 99–104, incorporated herein by reference. An appropriate Ullman Coupling reaction can be conducted according to Bryan E. Koene, et al., "Asymmetric Triaryldiamines as Thermally Stable Hole Transporting Layers for Organic Light Emitting Devices," Chemistry of Materials, Vol. 10, No. 8 (1998), also incorporated herein by reference.

Compound 2 is added to a dry, nitrogen-flushed vessel. Anhydrous methylene chloride is added and mixture is stirred and cooled in an acetone, dry ice bath. Excess boron tribromide in a methylene chloride solution is added dropwise, and the solution is heated to room temperature and stirred overnight. Solution is then removed and washed three times with sodium bicarbonate solution. The aqueous wash is then washed with methylene chloride twice, which is then added to the initial organic solution. The resulting solution is dried over calcium chloride, and reduced to dryness by rotary vacuum. Compound 3 is the crude product.

After purification, Compound 3 is used in the final reaction. 0.005 mole of Aluminum isopropoxide and 0.005 mole of 2-methyl-quinolinol is placed in a beaker along with 50 mL of anhydrous toluene. The mixture is heated and stirred until the bulk of the solids are dissolved. Solution is removed from heat, filtered, and placed in a nitrogen-filled flask. A solution of compound 3 (0.0022) mole and 0.005 mole of 2-methyl-8-quinolinol, dissolved in hot anhydrous toluene, is added to the flask.

The entire mixture is refluxed for 5 hrs, then allowed to cool and stirred overnight. Precipitate is filtered off and washed with ethanol and ether. Product is then dried under vacuum.

In the product 4, an amine functionality is interposed between the arylate group bonded to the aluminum atom, and the remainder of the quinacridone. This amine functionality serves to isolate the conjugation of the metal complex from the conjugation of the quinacridone.

An example of preparing an emissive material according to formula $(L_2M)_n$—X, where n is equal to 3 is given in Scheme 2 below:

Scheme 2
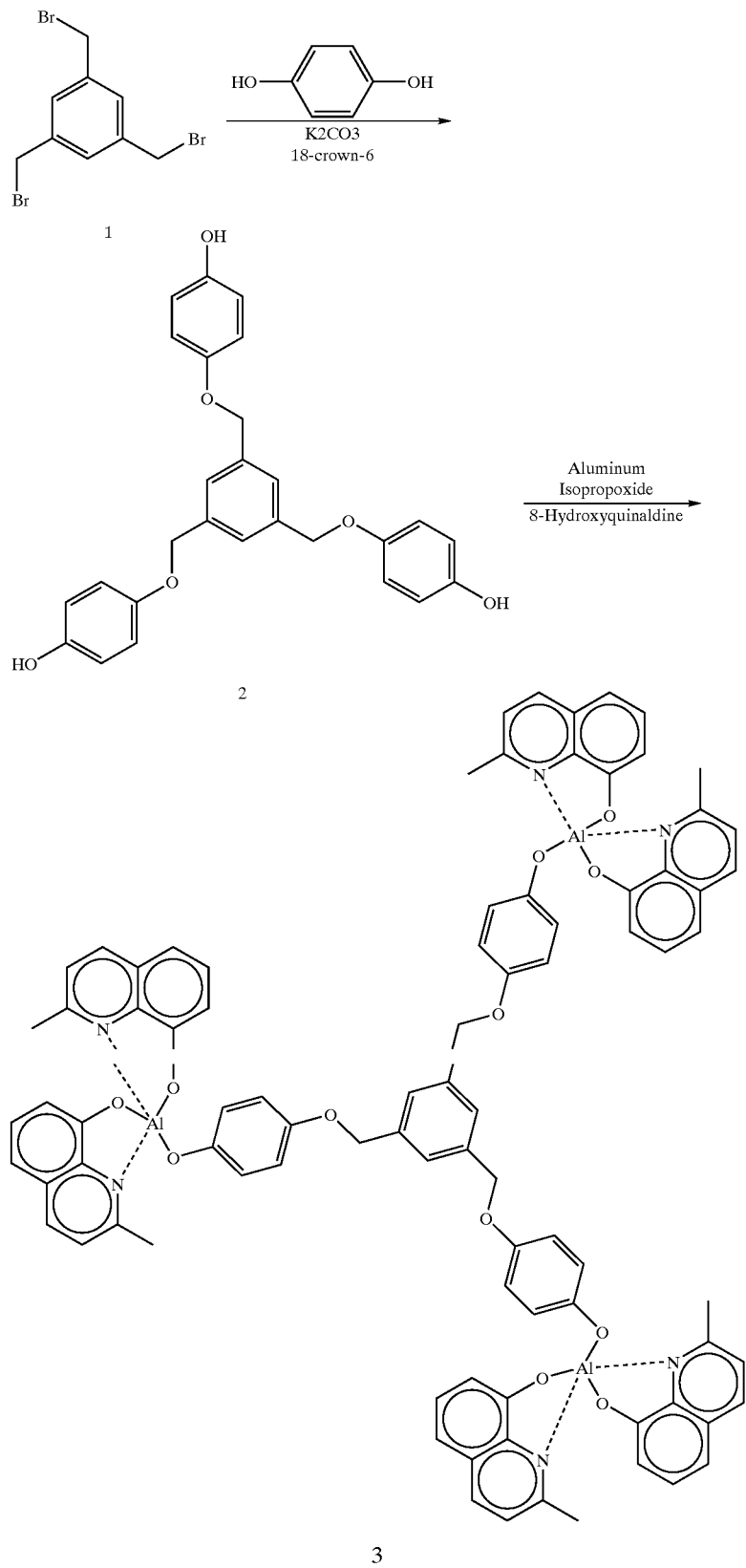

One equivalent of compound 1 is refluxed with 4 equivalents of 1,4-dihydroxybenzene, three equivalents of potassium carbonate, and about 0.1 equivalent of 18-Crown-6 ether in THF. After refluxing overnight, remaining salts can be removed by filtration, and the solution can be concentrated via rotary evaporation. The concentrated solution can be added to a solvent such as hexane, and the resulting precipitate is compound 2.

After purification, compound 2 is used in the final reaction. 0.005 mole of Aluminum isopropoxide and 0.005 mole of 2-methyl-quinolinol are placed in a beaker along with 50 mL of anhydrous toluene. The mixture is heated and stirred until the bulk of the solids are dissolved. Solution is removed from heat, filtered, and placed in a nitrogen-filled flask. A solution of compound 2 (0.0016) mole and 0.005 mole of 2-methyl-8-quinolinol, dissolved in hot, anhydrous toluene, is added to the flask.

The entire mixture is refluxed for five hours, then allowed to cool and stirred overnight. Precipitate is filtered off and washed with ethanol and ether. Product is then dried under vacuum.

The foregoing examples are for purposes of illustration only and are not to be deemed limiting of the invention which is defined by the following claims.

Compound 4 in Scheme 1 is expected to have the emission of the quinacridone branch, green or green-yellow.

Compound 4 in Scheme 2 is expected to have the emission of the aluminum quinolinolate complex, in the green-blue region.

We claim:
1. A light emissive material having structure

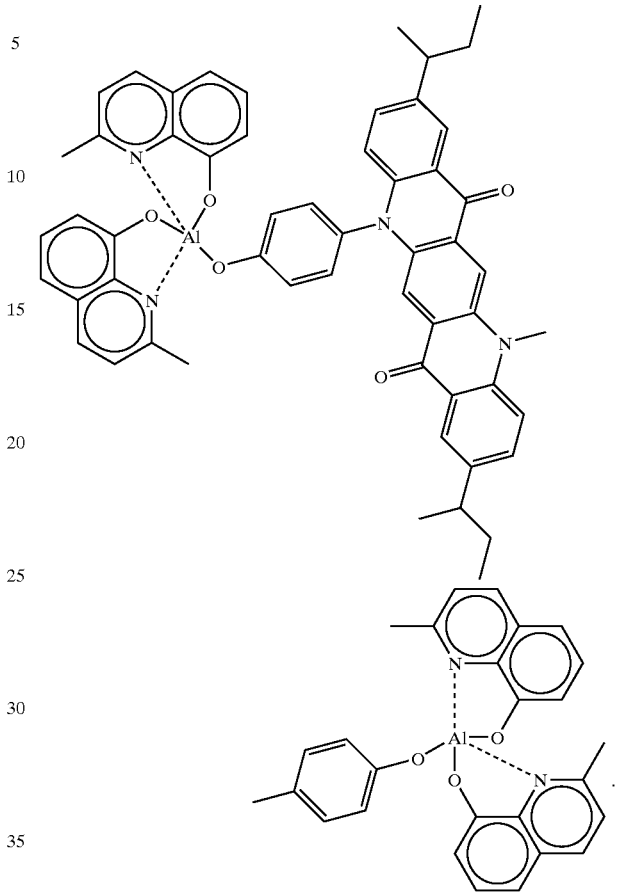

2. An organic light emitting device comprising:
an anode,
a cathode, and
at least one organic layer having an emissive layer,
wherein said emissive layer comprises a light emissive material according to claim 1.

* * * * *

UNITED STATES PATENT AND TRADEMARK OFFICE
CERTIFICATE OF CORRECTION

PATENT NO. : 6,803,125 B2
DATED : October 12, 2004
INVENTOR(S) : Travis P.S. Thoms et al.

It is certified that error appears in the above-identified patent and that said Letters Patent is hereby corrected as shown below:

Title page,
Item [75], Inventors, "Jiang-Ping Chen" should read -- Jian-Ping Chen --.

Column 1,
Line 66, "AlQ3" should read -- $AlQ_3$ --.

Signed and Sealed this

Twenty-sixth Day of April, 2005

JON W. DUDAS
*Director of the United States Patent and Trademark Office*